United States Patent [19]
Duffin et al.

[11] Patent Number: 5,752,976
[45] Date of Patent: May 19, 1998

[54] WORLD WIDE PATIENT LOCATION AND DATA TELEMETRY SYSTEM FOR IMPLANTABLE MEDICAL DEVICES

[75] Inventors: Edwin G. Duffin, New Brighton; David L. Thompson, Fridley; Steven D. Goedeke, Forest Lake; Gregory J. Haubrich, Champlin, all of Minn.

[73] Assignee: Medtronic, Inc., Minneapolis, Minn.

[21] Appl. No.: 494,218

[22] Filed: Jun. 23, 1995

[51] Int. Cl.$^6$ .................................................. A61N 1/37
[52] U.S. Cl. ............................................................ 607/32
[58] Field of Search ...................... 364/413.02; 128/903, 128/904, 696; 607/32, 60

[56] References Cited

U.S. PATENT DOCUMENTS

| | | |
|---|---|---|
| 3,253,588 | 5/1966 | Vuilleumier . |
| 3,910,257 | 10/1975 | Fletcher . |
| 3,972,320 | 8/1976 | Kalman . |
| 4,319,241 | 3/1982 | Mount . |
| 4,440,173 | 4/1984 | Hudziak . |
| 4,675,656 | 6/1987 | Narcisse . |
| 4,827,943 | 5/1989 | Bornn . |
| 4,889,131 | 12/1989 | Salem . |
| 4,981,141 | 1/1991 | Segalowitz . |
| 4,987,897 | 1/1991 | Funke . |
| 5,036,869 | 8/1991 | Inahara . |
| 5,113,869 | 5/1992 | Nappholz . |
| 5,336,245 | 8/1994 | Adams . |
| 5,381,798 | 1/1995 | Burrows . |
| 5,416,695 | 5/1995 | Stutman et al. ............... 364/413.02 |
| 5,417,222 | 5/1995 | Dempsey . |
| 5,593,426 | 1/1997 | Morgan et al. ............... 607/5 |

*Primary Examiner*—Scott M. Getzow
*Attorney, Agent, or Firm*—Harold R. Patton; Michael B. Atlass

[57] ABSTRACT

A system and method for communicating with a medical device implanted in an ambulatory patient and for locating the patient in order to selectively monitor device function, alter device operating parameters and modes and provide emergency assistance to and communications with a patient. The implanted device includes a telemetry transceiver for communicating data and operating instructions between the implanted device and an external patient communications control device that is either worn by or located in proximity to the patient within the implanted device transceiving range. The control device preferably includes a communication link with a remote medical support network, a global positioning satellite receiver for receiving positioning data identifying the global position of the control device, and a patient activated link for permitting patient initiated personal communication with the medical support network. A system controller in the control device controls data and voice communications for selectively transmitting patient initiated personal communications and global positioning data to the medical support network, for initiating telemetry out of data and operating commands from the implanted device and transmission of the same to the medical support network, and for receiving and initiating re-programming of the implanted device operating modes and parameters in response to instructions received from the medical support network. The communications link between the medical support network and the patient communications control device may comprise a world wide satellite network, hard-wired telephone network, a cellular telephone network or other personal communications system.

34 Claims, 6 Drawing Sheets

WORLD WIDE PATIENT LOCATION AND DATA TELEMETRY SYSTEM FOR IMPLANTABLE MEDICAL DEVICES

CROSS-REFERENCE TO RELATED APPLICATION

Reference is hereby made to commonly assigned, co-pending U.S. patent application Ser. No. (P-3071) for ADAPTIVE, PERFORMANCE-OPTIMIZING COMMUNICATION SYSTEM by S. Goedeke et al.

FIELD OF THE INVENTION

The present invention relates to communication systems for communicating with an implanted medical device or device system, and more particularly, such a communication system that may function on a world wide basis at any time to communicate patient location, device monitoring data, device re-programming data and to allow for effective response to emergency conditions.

BACKGROUND OF THE INVENTION

Over the years, many implantable devices have been developed to monitor medical conditions and deliver therapy to a patient. Such devices included electrical stimulation devices for stimulating body organs and tissue to evoke a response for enhancing a body function or to control pain, and drug delivery devices for releasing a drug bolus at a selected site. Other more passive implantable and wearable medical devices have been developed for monitoring a patient's condition.

Chronically implanted cardiovascular devices for monitoring cardiovascular conditions and providing therapies for treating cardiac arrhythmias have vastly improved patients quality of life as well as reduced mortality in patients susceptible to sudden death due to intractable, life threatening tachyarrhythmias. As implanted device technology has grown more sophisticated with capabilities to discover, monitor and affect more patient conditions (including otherwise life threatening conditions) patients have enjoyed freedom from hospital or home confinement or bed rest. However, the improved mobility brings with it the need to maintain communications with the patient and the implanted device.

Early in the development of cardiac pacemakers, patient follow-up to monitor pacemaker operation was facilitated by telephonic transmissions of skin surface ECGs in real time to a physician's office employing such systems as the MEDTRONIC™ TeleTrace™ ECG transmitter. Over time, various patient worn, ambulatory ECG and device monitors have been developed for providing ECG data for remote analysis of cardiac arrhythmias. Also, the remotely programmable modes of operation of implantable medical devices increased, and programming methods improved.

In current arrhythmia control devices, (e.g. cardiac pacemakers, and pacemaker-cardioverter-defibrillators) a relatively wide range of device operating modes and parameters are remotely programmable to condition the device to diagnose one or more cardiac arrhythmia and deliver an appropriate therapy. In cardiac pacemakers, the pacing rate in one or both heart chambers is governed by algorithms that process the underlying cardiac rhythm as well as physiologic conditions, e.g. patient activity level and other measured variables, to arrive at a suitable pacing rate. The pacemaker operating modes and the algorithm for calculation of the appropriate pacing rate are programmed or reprogrammed into internal memory by accessing the implanted pacemaker's telemetry transceiver with an external programmer. Even the diagnosis of a tachyrhythmia requiring delivery of a treatment therapy and the therapies to be delivered may now be governed by operating modes and algorithm parameters that can be programmed into and changed using such a programmer.

Such implanted devices can also process the patient's electrogram and any measured physiological conditions employed in the diagnosis and store the data, for subsequent telemetry out on interrogation by the external programmer. The telemetered out data is analyzed and may be employed to establish or refine the operating modes and parameters by a doctor to adjust the therapies the device can deliver. In general, the manner of communicating between the transceivers of the external programmer and the implanted device during programming and interrogating is referred to as telemetry.

Initially, when programming techniques were first devised, the paramount concern addressed related to patient safety. Safeguards addressed the concern that the patient could be put at risk of inadvertent mis-programming of the implanted device, e.g. by stray electromagnetic fields. For this reason, and in order to avoid high current consumption that would shorten the implanted device battery life, telemetry operating range was extremely limited. In systems continuing to the present time, telemetry has required application of a magnetic field at the patient's skin over the implanted device to close a reed switch while RF programming or interrogating commands are generated to be received by the implanted device transceiver. The programming or interrogating commands are decoded and stored in memory or used to trigger telemetry out of stored data and operating modes and parameters by the implanted device transceiver.

As stated at the outset, one of the rationales and attributes of implanted medical devices of the type described, is that the patient is allowed to be ambulatory while his medical condition is monitored and/or treated by the implanted medical device. As a further safety precaution, "programmers" (devices capable of programming all the operating modes or functions of the implanted device and for initiating interrogation through the telemetry system) are generally not provided to the patients. Patients are periodically examined and device interrogation is conducted by the physician using the external "programmer" during follow-up visits to the physicians office or clinic. This limits the frequency of monitoring and may require certain patients to remain close to the physician's office.

Emergency conditions (device failure, physiologic variable changes resulting in inappropriate therapy, transient conditions/problems) may require additional monitoring or follow-up.

The short range of conventional device telemetry is itself viewed as unduly limiting of a patient's mobility. In the medical monitoring field, longer range, continuously accessible telemetry has been sought and systems for doing so have been proposed. In U.S. Pat. No. 5,113,869 for example, an implanted ambulatory ECG patient monitor is described that is provided with longer range telemetry communication with a variety of external accessory devices to telemeter out alarm signals and ECG data and to receive programming signals. The high frequency RF signals are encoded, including the implanted device serial number, to ensure that the communication is realized only with the proper implanted device and that it is not misprogrammed.

Telemetry communication with other implanted devices, particularly drug infusion pumps or pacemaker-cardioverter-defibrillator devices, to initiate or control their operation is also disclosed. Communication between the implanted AECG monitor and an external defibrillator is also suggested through low current pulses transmitted from the defibrillator paddles through the body link in order to condition the implanted AECG monitor to provide telemetry signals to the external defibrillator.

One of the external devices disclosed in the '869 patent is a wrist worn, personal communicator alarm for responding to a telemetered out signal and emitting a warning to the patient when the implanted AECG monitor has detected an arrhythmia. The patient is thereby advised to take medications or contact the physician or to initiate external cardioversion. The personal communicator alarm also includes a transceiver and may also be used to control certain functions of the implanted AECG monitor. A further, belt worn "full disclosure recorder" is disclosed with high capacity memory for receiving and storing data telemetered out of the implanted AECG monitor when its memory capacity is exhausted.

A remote, external programmer and analyzer as well as a remote telephonic communicator are also described that may be used in addition to or alternately to the personal communicator alarm and/or the full disclosure recorder. The programmer and analyzer may operate at a distance to the implanted AECG monitor to perform programming and interrogation functions. Apparently, the implanted AECG may automatically transmit a beacon signal to the programmer and analyzer to initiate an interrogation function to transmit data to the programmer and analyzer on detection of an arrhythmia or a malfunction of the implanted AECG monitor detected in a self-diagnostic test. Or by setting a timer in the personal communicator alarm, the implanted AECG monitor may be automatically interrogated at preset times of day to telemeter out accumulated data to the telephonic communicator or the full disclosure recorder. The remote telephonic communicator may be part of the external programmer and analyzer and is automatically triggered by the alarm or data transmission from the implanted AECG monitor to establish a telephonic communication link and transmit the accumulated data or alarm and associated data to a previously designated clinic or physician's office through a modem.

The combination of external devices provided to a given patient is at the discretion of the physician. It is preferred that at least the patient be provided with the external programmer and analyzer including a communications link.

A similar programmer/interrogator for an implanted pacemaker-cardioverter-defibrillator device is disclosed in U.S. Pat. No. 5,336,245, wherein the data accumulated in the limited capacity memory implanted device is telemetered out to a larger capacity, external data recorder. The accumulated data is also forwarded to a clinic employing an auto-dialer and FAX modem resident in a personal computer-based, programmer/interrogator.

In each of these disclosed systems, presumably, the patient is able to communicate with the physician's office or clinic contemporaneously with the transmission of data by modem. In all such telemetry systems for programming an operating mode or parameter or interrogating accumulated patient data or device operating modes and parameters, the patient is located within a short range, typically within sight, of the remote devices, particularly the remote programmer. If the patient is out of range of the programmer and an attached telephone system, the security of the patient is diminished. Consequently, at risk patients are advised to remain close by to the programmer and telephone for their safety.

The performance over time of implanted medical devices in the implant population is informally monitored by the periodic patient follow-ups employing the telemetry system conducted by the physician and the reporting of device malfunctions from the physician to the device manufacturer. Moreover, operating algorithm improvements developed over time to counter adverse device performance reports or to simply improve device function are provided to physicians to employ in re-programming the implanted devices at the next patient follow-up.

Although significant advances have been made in allowing patient's who are dependent on implanted medical devices to be ambulatory and still allow for monitoring of the device operation or the patient's underlying condition, a need remains to expand patient security while allowing the ambulatory patient to range widely. Telemetry systems in current use require prepositioning of the telemetry head over the implanted medical device, although the telemetry systems described above may offer the possibility of telemetry at a distance of several meters. In any case, such telemetry systems cannot communicate patient device information (uplink telemetry) or accept re-programming (downlink telemetry) when the patient is in remote or unknown locations vis-a-vis the physician of medical support network. In certain patient conditions, the inability to communicate with the medical implant can significantly increase patient mortality or cause serious irreversible physical damage.

SUMMARY OF THE INVENTION

It is therefore an object of the present invention to provide a patient data communication system for world wide patient location and data and re-programming telemetry with a medical device implanted in the patient.

It is a further object of the present invention to address the above described problems by providing such a communication system allowing the device and/or patient to communicate with support personnel at any time and from any place.

It is a still further object of the invention to allow the medical device and patient to be accurately and automatically located enabling prompt medical assistance if necessary.

These and other objects of the invention are realized in a first aspect of the invention in a system for communicating patient device information to and from a medical device implanted in an ambulatory patient and with a remote medical support network comprising: an implanted device telemetry transceiver within the implanted medical device for communicating data and operating instructions to and from the medical device in a coded communication, the implanted device telemetry transceiver having a transceiving range extending outside the patient's body a predetermined distance sufficient to receive and transmit coded telemetry communications at a distance from the patient's body; and an external patient communications control device adapted to be located in relation to the patient within the device transceiving range having a system controller for facilitating communications, an implant wireless interface including a control device telemetry transceiver for receiving and transmitting coded communications between the system controller and the implant device telemetry transceiver, a global positioning system coupled to said system controller for providing positioning data identifying the global position of the patient to the system controller; communications means for communicating with the remote medical support network; and communications network interface means coupled to the system controller and the communications means for selectively enabling the communications means for transmitting the positioning data to the medical support network and for selectively receiving commands from the medical support network.

Preferably the system further comprises an external patient communications device adapted to be located in relation to the patient within the device transceiving range for providing patient voice and data communications with the system controller, so that patient voice communications may be effected through the communications interface means and the communications means with the remote medical support network.

Furthermore, the communications interface means may effect two-way communication of voice and/or data between the remote medical support network and the patient communications device and implanted device telemetry transceiver by inclusion of cards for accessing one or all of the communications means including a cellular telephone network and a satellite-based telecommunication network, a hard-wired telephone communications system and/or a hard-wired interface for computer based system for local area and for modem-based e-mail communications systems. The cards are preferably interchangeable to fit the application needed by the particular patient.

The communications interface means preferably include two-way voice communications between the patient and the medical support network and two-way data communications for selectively receiving interrogation or programming commands from the medical support network to interrogate or program the operation of the device operation and to interrogate patient location.

The present invention allows the residential, hospital or ambulatory monitoring of at-risk patients and their implanted medical devices at any time and anywhere in the world. The medical support staff at a remote medical support center may initiate and read telemetry from the implanted medical device and reprogram its operation while the patient is at very remote or even unknown locations anywhere. Two-way voice communications with the patient and data/ programming communications with the implanted medical device may be initiated by the patient or the medical support staff. The location of the patient and the implanted medical device may be determined and communicated to the medical support network in an emergency. Emergency response teams can be dispatched to the determined patient location with the necessary information to prepare for treatment and provide support after arrival on the scene.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

Figure 1:
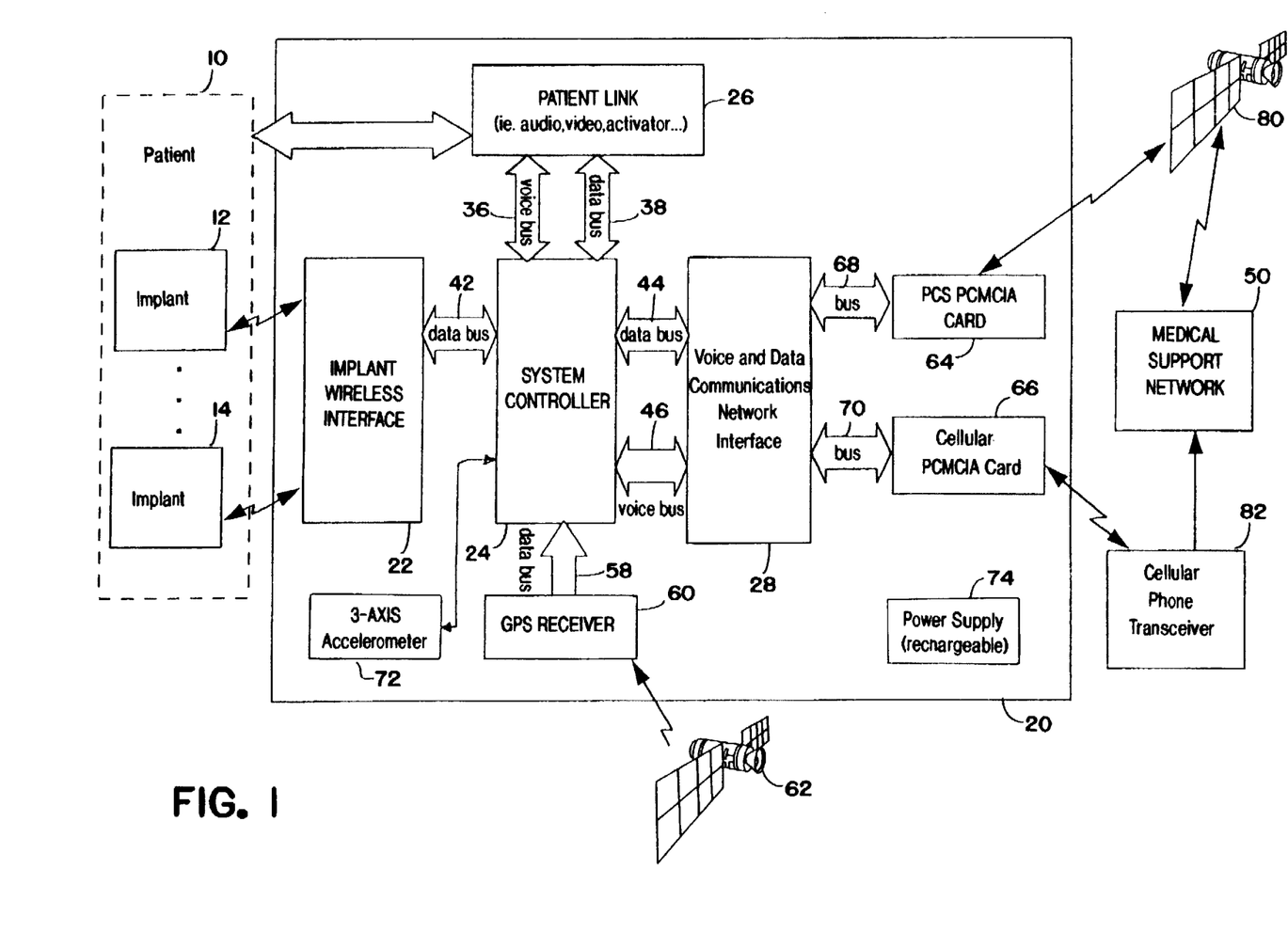
FIG. 1 is block level diagram of a first variation of the system of the invention for a patient having free ranging mobility including an implantable medical device, a patient communications control device and a medical support network optionally employing wireless satellite telecommunication and a global positioning satellite receiver.
Figure 2:
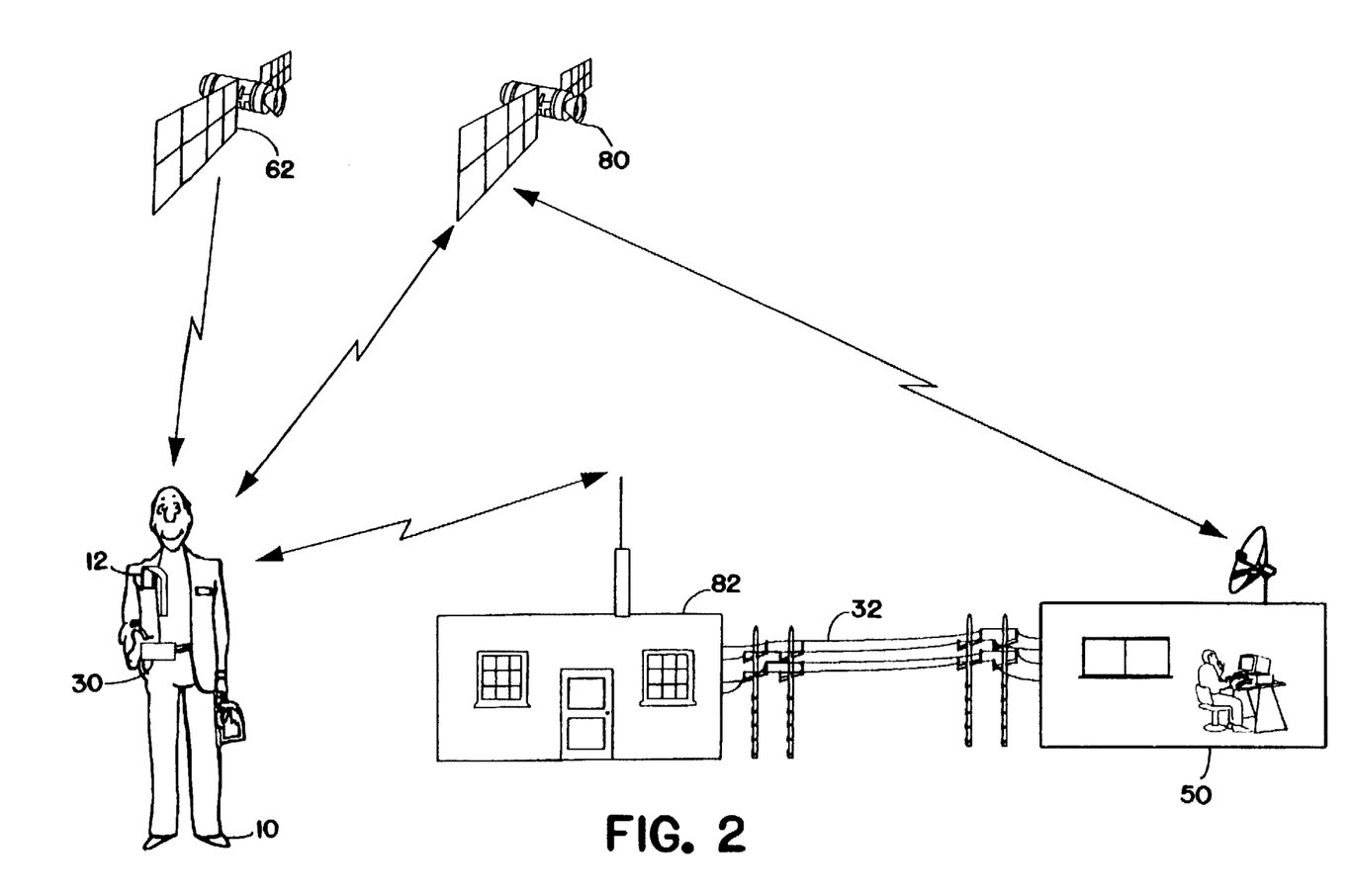
FIG. 2 is a schematic illustration of the system of FIG. 1 in relation to a patient.

The Global Communications and Monitoring System (GCMS) of the present invention provides a means for exchanging information with and exercising control over one or more medical devices implanted within the body of a patient employing the patient communications control device. The GCMS in its most comprehensive form of FIGS. 1 and 2 is intended to function no matter how geographically remote the patient may be relative to the monitoring site or medical support network. In this form, the GCMS provides an alarm to notify the medical support network should device or patient problems arise, determines patient location via the Geopositioning Satellite System (GSS), and allows verbal communication between the patient and monitoring personnel via a cellular telephone system link (if available at the patient location) or a satellite based telecommunications link if the patient is outside the range of a cellular link or subscribes only to the satellite-based link.

The system is not intended to be limited to such remote use by a free ranging patient and is intended to also be used when the patient is less mobile. In the sub-system or second variation illustrated in FIGS. 3-5, the patient communication control device is intended to be coupled to a telephone or other communications system for a patient with more limited mobility. For example, the standard telecommunications system may be accessed either through a hard-wired link or by a cordless telephone with a telephone receiver in the room attached to a phone jack. In this case, the cellular or satellite-based telecommunications interface capabilities are not necessary, and the GSS capability may be superfluous.

Figure 4:
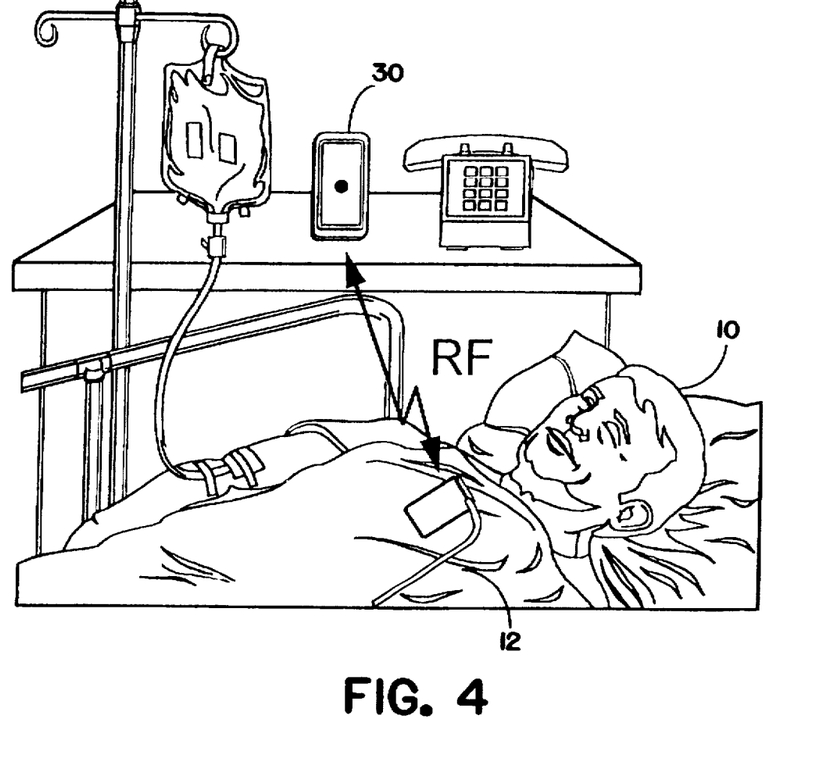
FIG. 4 is a schematic illustration of the system of FIG. 3 in a line powered monitor for use in a patient's hospital room.
Figure 5:
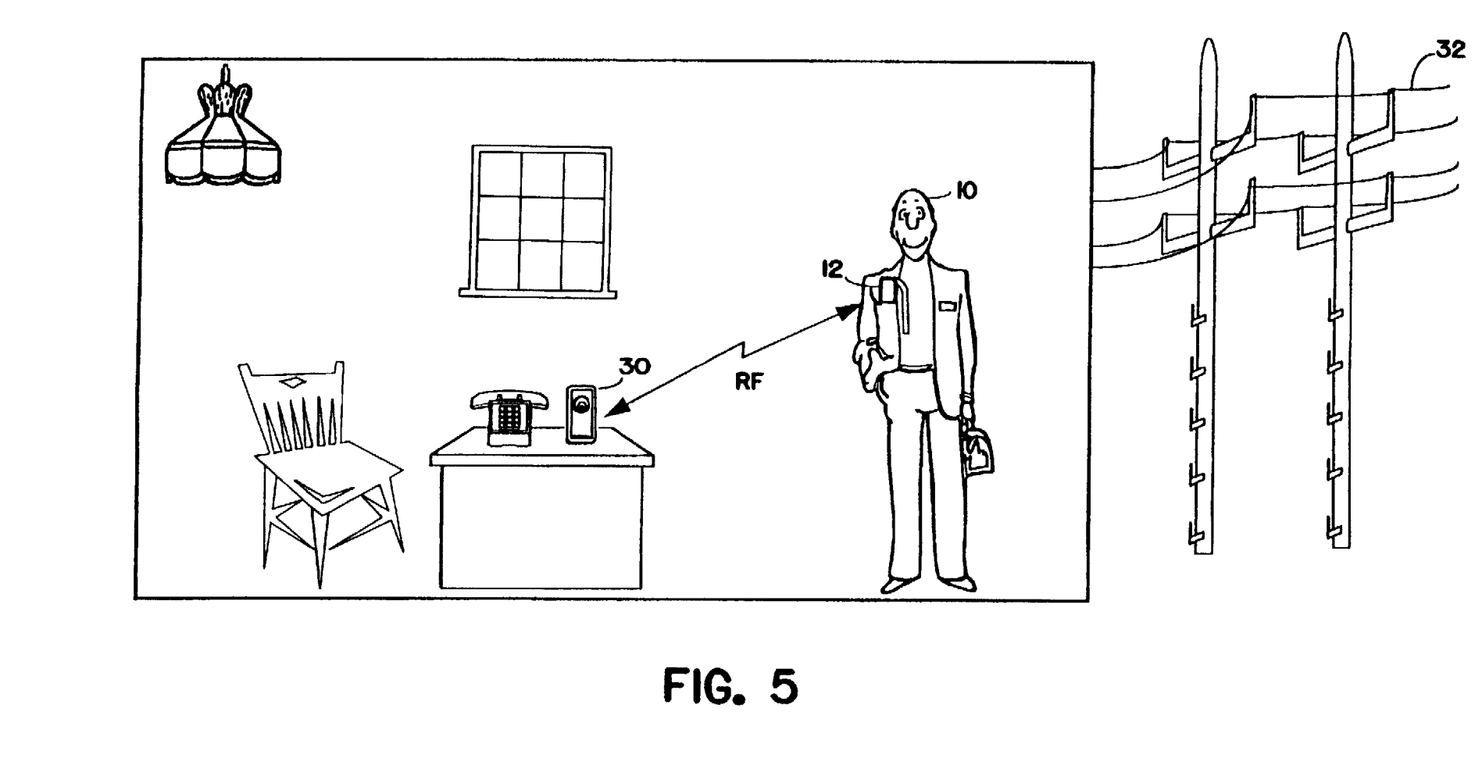
FIG. 5 is a schematic illustration of the system of FIG. 3 employing a patient-worn, communications link and a line powered monitor for use in a patient's home.

Preferably, the GCMS of FIG. 1 includes all of these capabilities embodied in a patient communications control device that is small and light enough to be attached to the patient when the patient is mobile or to be used by the patient as a free standing unit at the patient's residence or hospital room. Alternatively, as shown in FIGS. 3-5, the GCMS can be re-configured in part as a stand alone, line powered, room monitor and the remaining part can be implemented as a patient-worn, battery powered, communications link with a transceiver capable of two-way communication between the patient, the implanted medical device and the line powered monitor.

Figure 3:
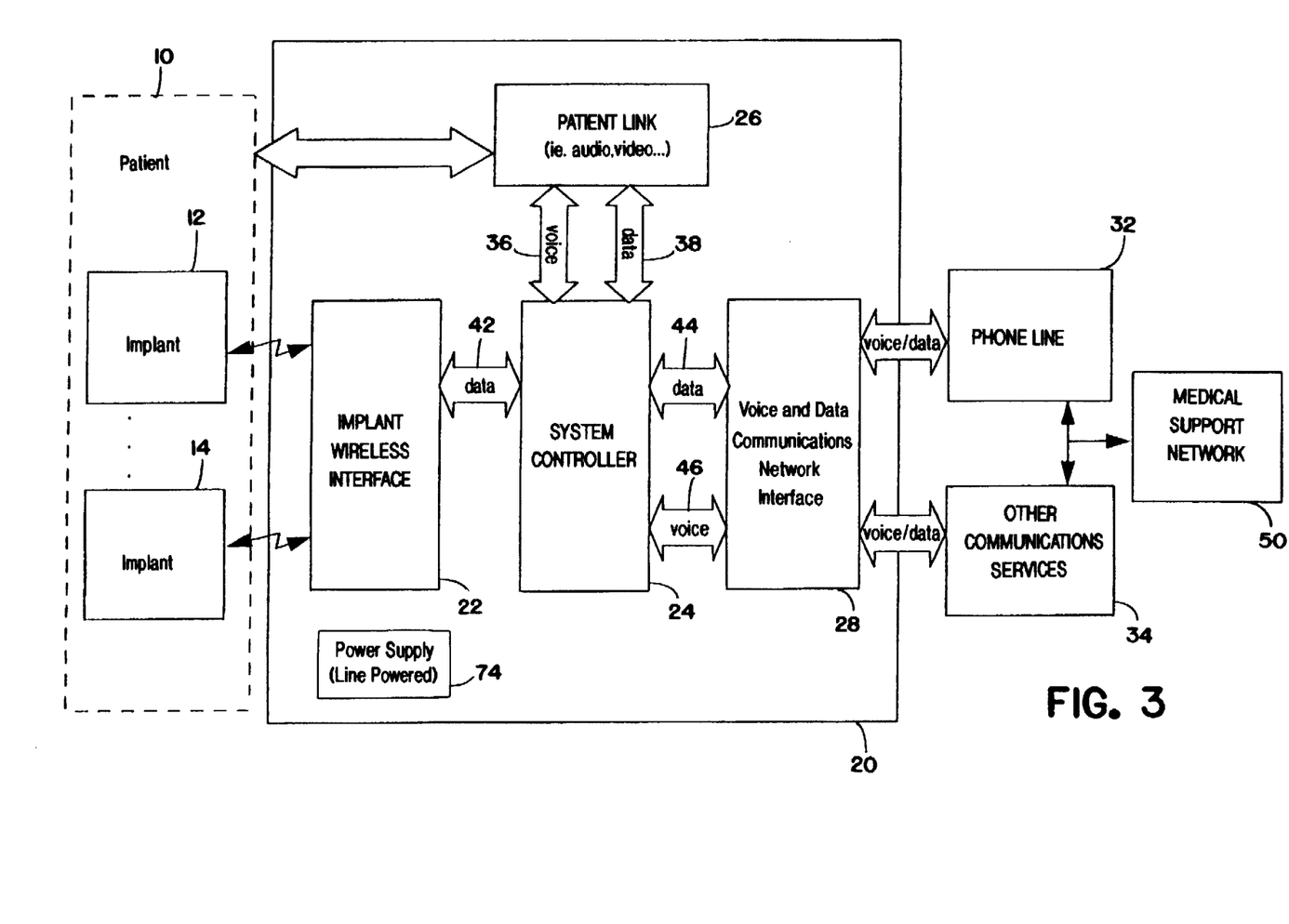
FIG. 3 is block level diagram of a second variation of the system of the invention for a patient having limited mobility including an implantable medical device, a patient communications control device and a medical support network employing conventional wired telecommunication.

FIGS. 1 and 3 are intended to show the alternate components of both of the variations of the GCMS, although the alternate components may be included in the same GCMS. The patient 10 has one or more implanted medical devices 12, 14, which in the latter case may communicate with one another is known as, for example, using the body medium in a manner described in commonly assigned U.S. Pat. No. 4,987,897 to Funke. The medical device 12 (and associated device 14, if present) may be, for example, an arrhythmia control device, e.g. a cardiac pacemaker or a pacemaker-cardioverter-defibrillator. A relatively wide range of device operating modes and parameters are remotely programmable to condition such a device 12 to diagnose one or more conditions such as cardiac arrhythmias and/or deliver electrical or other stimulus appropriate for therapy. The implanted medical device 12 may alternatively be a drug administration device, cardiomyoplasty device, neural stimulator or any other implantable device with electronic control functions that can be programmed and/or have memory for storing patient and device operating data.

At least one implanted medical device 12 possesses a transceiver of the type known in the art for providing two-way communication with an external programmer. The encoded communication may be by the RF transmission system such as is described in the above-referenced '869 patent or by using spread spectrum telemetry techniques described in U.S. Pat. No. 5,381,798 to Burrows or by the system disclosed in the above-referenced (P-3071) application or any of the known substitutes. The telemetry technique employed and the transceiver of the implanted medical device 12 have enough range to communicate between the transceiver in the implant wireless interface 22 in the remote patient communications control device 20 and the implant (12 . . . 14). The system disclosed in the above-referenced (P-3071) application may be employed to increase the accuracy and efficiency of the uplink and downlink telemetry.

Figure 6:
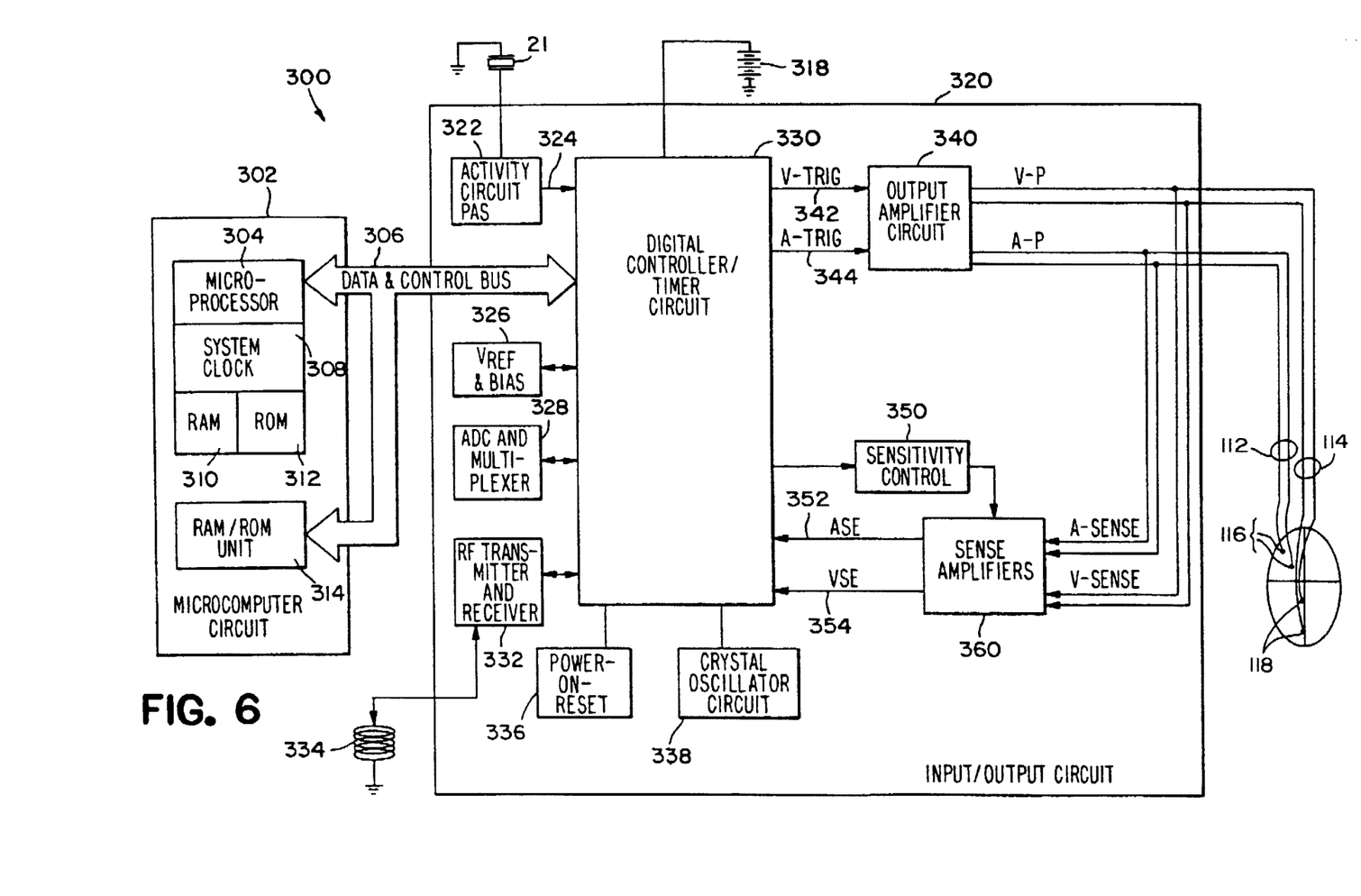
FIG. 6 is a block diagram of an exemplary implanted medical device with which the invention may be practiced.

FIG. 6, depicts an implantable pulse generator (IPG) circuit 300 and atrial and ventricular lead system 112, 114 having programmable modes and parameters and a telemetry transceiver of a DDDR type known in the pacing art as an example of an implanted medical device 12. While described in some detail, this device 12 provides only one example of the kind of implantable device that may be employed with this invention.

The IPG circuit 300 of FIG. 6 is divided generally into a microcomputer circuit 302 and a pacing circuit 320. The pacing circuit 320 includes the output amplifier circuit 340 and the sense amplifiers 360. The output circuit 340 and sense amplifier circuit 360 may contain pulse generators and sense amplifiers corresponding to any of those presently employed in commercially marketed cardiac pacemakers for atrial and ventricular pacing and sensing. The bipolar leads 112 and 114 are illustrated schematically with their associated electrode sets 116 and 118, respectively, as coupled directly to the input/output circuit 320. However, in the actual implanted device they would, of course, be coupled by means of removable electrical connectors inserted in a connector block.

Sensed atrial depolarizations or P-waves that are confirmed by the atrial sense amplifier (ASE) in response to an A-sense are communicated to the digital controller/timer circuit 330 on ASE line 352. Similarly, ventricular depolarizations or R-waves that are confirmed by the ventricular sense amplifier in response to a V-sense are communicated to the digital controller/timer circuit 330 on VSE line 354.

In order to trigger generation of a ventricular pacing or VPE pulse, digital controller/timer circuit 330 generates a trigger signal on V-trig line 342. Similarly, in order to trigger an atrial pacing or APE pulse, digital controller/timer circuit 330 generates a trigger pulse on A-trig line 344.

Crystal oscillator circuit 338 provides basic timing clock for the pacing circuit 320, while battery 318 provides power.

Power-on-reset circuit 336 responds to initial connection of the circuit to the battery for defining an initial operating condition and may reset the operative state of the device in response to a low battery condition. Reference mode circuit 326 generates stable voltage and current references for the analog circuits within the pacing circuit 320. Analog to digital converter (ADC) and multiplexor circuit 328 digitizes analog signals. When required the controller circuit will cause transceiver circuit 33 to provide real time telemetry if a cardiac signals from sense amplifiers 360. Of course, these circuits 326, 328, 336, and 338 may employ any circuitry similar to those presently used in current marketed implantable cardiac pacemakers.

Data transmission to and from the external programmer of the patient communications control device of the preferred embodiment of the invention is accomplished by means of the telemetry antenna 334 and an associated RF transmitter and receiver 322, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as is well known in the pacing art. The IPG transceiver system disclosed in the above-referenced (P-3071) application may be employed to provide the uplink and downlink telemetry from and to the implanted medical device in the practice of the present invention.

Control of timing and other functions within the pacing circuit 320 is provided by digital controller/timer circuit 330 which includes a set of timers and associated logic circuits connected with the microcomputer 302. Microcomputer 302 controls the operational functions of digital controller/timer 324, specifying which timing intervals are employed, and controlling the duration of the various timing intervals, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-trig, V-trig, ASE and VSE signals. The specific values of the intervals defined are controlled by the microcomputer circuit 302 by means of data and control bus 306 from programmed-in parameter values and operating modes.

If the IPG is programmed to a rate responsive mode, the patient's activity level is monitored periodically, and the sensor derived V-A escape interval is adjusted proportionally. A timed interrupt, e.g., every two seconds, may be provided in order to allow the microprocessor 304 to analyze the output of the activity circuit (PAS) 322 and update the basic V-A escape interval employed in the pacing cycle. The microprocessor 304 may also define variable A-V intervals and variable ARPs and VRPs which vary with the V-A escape interval established in response to patient activity.

Digital controller/timer circuit 330 thus defines the basic pacing or escape interval over a pacing cycle which corresponds to a successive A-V interval and V-A interval. As a further variation, digital controller/timer circuit 330 defines the A-V delay intervals as a SAV that commence following a sensed ASE and a PAV that commences following a delivered APE, respectively.

Digital controller/timer circuit 330 also starts and times out intervals for controlling operation of the ASA and VSA in sense amplifier circuit 360 and the APG and VPG in output amplifier circuit 340. Typically, digital controller/timer circuit 330 defines an atrial blanking interval following delivery of an APE pulse, during which atrial sensing is disabled, as well as ventricular blanking intervals following atrial and ventricular pacing pulse delivery, during which ventricular sensing is disabled. Digital controller/timer circuit 330 also defines an atrial refractory period (ARP) during which atrial sensing is disabled or the ASE is ignored for the purpose of resetting the V-A escape interval. The ARP extends from the beginning of the SAV or PAV interval following either an ASE or an A-trig and until a predetermined time following sensing of a ventricular depolarization or triggering the delivery of a VPE pulse as a post-ventricular atrial refractory period (PVARP). A ventricular refractory period (VRP) may also be timed out after a VSE or V-trig. The durations of the ARP, PVARP and VRP may also be selected as a programmable parameter stored in the microcomputer 302. Digital controller/timer circuit 330 also controls sensitivity settings of the sense amplifiers 360 by means of sensitivity control 350.

The illustrated IPG block diagram of FIG. 6 is merely exemplary of one form of an implanted medical device 12 having a telemetry transceiver. The telemetry transceiver 332 is capable of receiving interrogation commands for uplink telemetry of accumulated data, e.g. stored histograms of EGM data maintained in RAM 310 or RAM/ROM unit 314, or of real-time data, e.g. the raw EGM of the patient's heart. In addition, it is capable of receiving permanent reprogramming commands or certain temporary programming commands for changing operating modes or parameters of the IPG 300 to counter a condition diagnosed by the medical support network. In this manner, the selective initiation of the operation of the therapeutic treatment (pacing for device 12) and monitoring can be effected through operating commands received by said implanted device telemetry transceiver 322. Furthermore, the operating algorithms governing the various pacing modes or parameters of those operating algorithms may be re-checked and altered through downlink interrogation and re-programming. In addition, the normal, periodic follow-up of the IPG 300 operation can be remotely initiated and conducted using the uplink and downlink telemetry between the transceiver 332 and the implant wireless interface under the control of the system controller as described below. The present invention can therefore readily be practiced using the basic hardware of existing microprocessor-controlled, dual chamber pacemakers, pacemaker-cardioverter-defibrillators and other medical devices, with a transceiver capable of uplink and downlink telemetry at a distance of up to several meters between the telemetry antenna 334 and the external telemetry antenna of the patient communications control device 20 or 20' of the variations of the present invention.

Returning to FIGS. 1 and 3, the patient communications control device 20, 20' therefore includes the implant wireless interface 22 that operates as a two-way telemetry transceiver for communicating with the telemetry transceiver of the implanted medical device 12 or devices 12, 14 and is controlled in those operations by a microcomputer-based system controller 24, preferably a 486XX microprocessor with RAM and ROM, e.g. the Cardio 486 available from SMOS SYSTEMS located in San Jose, Calif. maybe employed as the controller 24. The system controller 24 contains a system clock for maintaining an accurate time base which in one embodiment may be recalibrated periodically via accurate clocks in the GPS satellites 62. The microcomputer-based system controller 24 is coupled to the patient link 26 and the voice and data communications network interface 28 via voice and data buses 36 and 38. A patient link 26 provides a microphone and speaker through which the patient 10 can use for voice communication through the system controller 24 and the voice and data communications network interface 28 with the remote medical support network 50. Communication between the system controller 24 and the communications interface 28 is via data and voice buses 44 and 46. The system controller 24 may be part of a standard or modified cellular telephone or other personal communication device and may simply recognize specific telemetered signals from the implanted device if desired.

At the medical support network 50, a base station is provided to be in the communication link with the monitor 30 or the patient-worn communications device 40. The base station is preferably a microprocessor-based system that includes the software and hardware needed for voice communication with the patients to locate the patient and to interrogate and program the implanted medical devices using the communications interface links incorporated into the GCMS.

Patient voice communications through the patient link 26 include both actual patient voice and/or manually actuated signalling which may convey an emergency situation. For example, a patient may initiate communications through link 26 by depressing a button and/or speaking into the microphone/speaker. The patient voice is converted to an audio signal, digitized, encoded and transmitted either by voice bus 36 or by a transceiver in the case where the patient link 26 is physically separated from the system controller 24, as described below. The patient activated emergency signal is likewise encoded and transmitted by data bus 38 or its equivalent transceiver encoded RF signal to the system controller 24. Patient link 26 is a custom designed circuit that preferably has a microphone and speaker, associated drivers, a visual indicator (i.e. light or LCD display), and a patient activator. In the embodiment where the patient link 26 is physically part of the patient communications control device 20, the patient link also includes interface circuitry to buses 36 and 38 as shown in FIG. 1. Alternatively, the patient link 26 can be combined with the implant wireless interface as a combined PCMCIA (or other communications) card and a single data bus may be shared between the two circuits. In a further embodiment having a physically separated and separately powered patient communications control device 26, the voice and data buses 36 and 38 can be replaced by short-range wireless LAN PCMCIA cards at each end of the link. An infrared wireless LAN PCMCIA adaptor with an integrated transceiver, Model No. 87G9743, is currently available from IBM, Inc., Somers, N.Y. An RF wireless LAN PCMCIA adaptor with an integrated transceiver, Model No. 80G0900 is also available from IBM, Inc., Somers, N.Y. Other similar devices may be used.

Continuing specifically with the first variation of FIGS. 1 and 2, these figures depict the components of the more comprehensive GCMS of the present invention for allowing greater patient mobility, a wider range of communications network interface links and the capability of locating the patient anywhere in the world. In the GCMS of FIG. 1, all components of patient communications control device 20 are incorporated into the patient-worn communications device 40 which may be worn, for example, on a patient's belt or carried in a pocket, or worn on a wrist. Alternatively, as described above, the patient link 26 may be separated into a wrist-worn device having a separate transceiver for convenience of use in voice communication. In any event, the emerging Personal Communications System (PCS) technology may be employed in the miniaturization of the system components.

In accordance with one aspect of the invention, the system controller 24 is coupled to a GPS receiver 60 via bus 58 for receiving patient positioning data from an earth satellite 62. The GPS receiver 60 may use current systems such as the Mobile GPS™ (PCMCIA GPS Sensor) provided by Trimble Navigation, Inc. of Sunnyvale, Calif. or Retki GPS Land Navigation System provided by Liikkura Systems International, Inc. of Cameron Park, Calif., or other similar systems. The GPS receiver 60 may be actuated by a command received through the system controller 24 from the medical support network, in the case of an emergency response. In the case of a non-emergency, periodic follow-up, the GPS receiver 60 may be enabled once an hour or once a day or any other chosen interval to verify patient location. The determined location may be transmitted to the medical support network and/or stored in RAM in the system controller 24. To maintain patient location information in the absence of GPS signals (such as inside metal buildings), a three-axis accelerometer 72 or other position/motion determining device can be incorporated into the system. By knowing original position (from the last valid GPS point), time (from the internal clock) and acceleration (motion), patient position can be calculated from the three axis coordinates realized from each accelerometer output calculated in each case from:

$$x(t) = x(0) + v(0)t + \int \int a(t)dt$$

where x(0) is the initial position stored in memory for each axis, t is time, a is acceleration and v is velocity.

In the free ranging embodiment of FIGS. 1 and 2, two communication network interface links with the medical support network 50 are included, although the communication interface links of the second variation of FIGS. 3–5 may be included for optional home use. One non-hard-wired communication interface link is effected through the soon to be deployed, worldwide satellite communications system, called "Iridium", by Motorola, Inc. of Schaumburg, Ill. This is a PCMCIA card 64 which may be built from common components by one skilled in the art. Another (second) communications link can be effected by the ARDIS (Advanced Radio Data Information Service) pocket radio communications network via PCMCIA link card 66, a Mobidem modem available from Ericsson, Inc. of Raleigh, N.C. Both of the radio links operate as modems with voice and data simultaneously transmitted via adding the CT8020 (DSP Group of Santa Clara, Calif.) to a standard data modem such as a 28.8 Keepintouch™ Express modem from AT & T Corp. of Largo, Fla.

Either or both PCMCIA cards 64 and 66 may be provided and they are coupled with the voice and communications network 28 via buses 68 and 70, respectively. When both are provided, access to the communications satellite link 80 is automatically obtained when a link to a cellular transceiver 82 is not possible.

It should be noted that "Iridium" manages cellular location of each subscriber in the network at all times. The subscriber unit, which in this invention would be incorporated into the device 20 (or communicatively connected to it) identifies itself and its location on a periodic basis to the system manager. In any system chosen it is expected that the control and communications device will have to report in to a management system regarding its location on a periodic or at least on a changed location basis or both. The implanted device need not be concerned about this activity and need not use any of its battery power to accomplish it since only the external device 20 (in the preferred embodiments) needs to be involved in such location communication. Only by knowing the patient location can the medical system 50 communicate to the implanted device at any time it wants or needs to. Accordingly, if emergency communications are expected short intervals between reporting in are recommended.

By checking in, the patient's external communications device would act like a cellular phone, answering incoming medical system messages broadcast into the cell in which it is located.

For patient convenience, a personal communicating device may incorporate the controller/communicator that communicates between implanted device(s) and the external world. In this way it could look like and operate as a personal communicator or cellular phone and reduce patient psychological discomfort. It should also be recognized that if the cellular telephone system manages all communication functions between the outside-the-patient-system and the medical community system, the implanted device need only be able to communicate with the cellular communications product.

FIG. 2 illustrates the free ranging patient 10 located remotely from the medical support network 50 and from any hard-wired communications link. The patient communications control device 20 is implemented in the belt-worn portable unit 40, although the patient link 26 may be worn separately on the patient's wrist (not shown). Alternatively, the patient communications control device 20 including the patient link 26 may be packaged into a portable telephone configuration and carried in a pocket. In any embodiment, the patient location may be determined by communications with the GPS 62. The voice and data communications link with the medical support network 50 may be effected by a cellular phone link including transceiver 82. Alternatively, the voice and data communications link may be effected using the communications satellite link 80.

The patient communications control device 20 of FIGS. 1 and 2 is powered by a battery power supply 74 that preferably is rechargeable. The system controller 24 includes a power control system for powering down the microprocessor and the associated components of the patient communications control device 20 except on receipt of an interrupt in a manner well known in the art.

Power consumption can be significantly reduced by powering up the communication and satellite circuitry periodically for a short period of time to re-acquire a GPS location and/or look for requests for data or status from the medical support network 50. This system power consumption reduction can greatly enhance battery lifetime requiring less frequent battery replacement or recharging, in the case of a rechargeable battery configuration. As an alternate to using a management system to maintain a patient location data based on patient's device periodic check-in each GCMS system for each patient could have a specific time slot (for example, 30 seconds) non-overlapping with other GCMS systems to power up, acquire location coordinates from the GPS system and be alert for a call from the medical support network 50. Periodically (for example, once per week), the medical support network 50 would reset/recalibrate the system clock in system controller 24 from the atomic clock in the GPS satellite system. This would ensure that no specific GCMS system clock would drift out of range of its allotted time slot and be unavailable for reception or drift into an adjacent time slot. Other time dividing schemes used in other arts may also be employed to maximize battery life for any system.

Turning to the second variation of the invention illustrated in FIGS. 3–5, it should be noted that the system of FIG. 1 may also be used in the home or in the hospital using the cellular communications link card 66. However, the modified patient communications control device 20' of FIG. 3 is preferably implemented with the voice and data communications network interface 28 having the capability of directly linking with a hard-wired phone line 32 or other communication services, which may include a hospital installed network, e.g. a personal computer interface to a local area network. In either case, the modified patient communications control device 20' may be implemented in a number of portable or stationary monitor 30 forms.

In the embodiment illustrated in FIG. 4, all of the FIG. 3 components of the modified patient communications control device 20' are located in the monitor 30. The patient link 26 and the implant wireless interface 22 are hard-wired by voice and data buses 36, 38 and 42 to the system controller 24. In the embodiment of FIG. 5, the patient link 26 and the implant wireless interface 22 are located in the patient-worn communications device 40. The remaining components of the modified patient communications control device 20' are located in monitor 30, and suitable RF telemetry transceiver links are substituted for the buses 36, 38 and 42. In either embodiment, the power supply 74 of the monitor 30 may be line powered. The modified patient communications control device 20' within monitor 30 may also be coupled to a wall jack for hard-wired communications through the phone line 32 or other communications service 34 with a medical support network 50 located remotely or within the hospital.

As described above, implantable devices such as 12 . . . 14 include telemetry transceivers with range suitable for communicating over a short range to the implant wireless interface 22 of the modified patient communications control device 20' within stand alone monitor 30. This remote link offers advantages over patient-worn electrodes or programming heads required in the standard skin contact telemetry and monitoring used at present. Skin contact is difficult to maintain, as the adhesive for the electrodes or heads fails in time, skin irritation is often a problem and inadvertent removal of electrodes is also prevalent. Moreover, the EGM and other body condition monitoring capabilities of advanced implanted medical devices can be taken advantage of to substitute for in-hospital monitoring, e.g. Holter monitoring of the patient's electrogram. The electrogram and/or other sensor derived data, e.g. pressure, temperature, blood gases or the like, stored by the implanted device can be transmitted out continuously or on periodic automatic telemetry command and sent by the communications link to the remote or hospital medical support network 50.

In either environment of FIG. 4 or 5, the patient 10 may communicate with the medical support staff at the medical support network 50 through the voice channel provided in the patient link 26. The patient communications control device 20 or 20' in either embodiment can retrieve all implanted device stored patient and device operating data on receipt of a command from the medical support network 50, process and temporarily store such data, and transmit it back to the support network 50 for analysis. Moreover, implanted devices 12 . . . 14 may be reprogrammed from the medical support network 50 to alter device operating modes and parameters employing the modified patient communications control device 20' as a programmer. Finally, the modified patient communications control device 20' can transmit an alarm to the medical support network should there be problems with the patient or implanted devices 12, 14. For example, the implanted devices 12, 14 may signal a low battery condition or a low drug supply in the case of an implanted drug dispenser or other problems found in self-diagnostic routines periodically conducted within the implanted devices 12 . . . 14.

The variations and embodiments of the GCMS of the present invention provides comprehensive monitoring of implanted medical devices independent of the geographic mobility of the patient using the devices, obviating the need for the patient to return to a designated follow-up monitoring site or clinic. Moreover, it allows determination of the patient's geographic location via the GSS 62 while providing simultaneous two-way communication with devices and the patient when desired.

In addition to emergency response and routine patient management, the GCMS facilitates medical device clinical studies, providing data collection at one central site from all study patients without requiring their active involvement or clinic visits. This is especially useful for conducting government-mandated post-market surveillance studies. Should there be need to upgrade or change the behavior of implanted devices the global system allows a central monitoring site to revise all involved implants anywhere in the world by transmitting new programming instructions to every device (assuming appropriate governmental authorities and the patients' physicians have agreed to the need for such changes). The patient need not be directly involved in this updating and need not be aware of the actual process.

A continuous and automatic medical monitoring service could be implemented to shorten response time for emergency medical situations or device events signifying patient difficulty. For example, a patient having an implanted cardioverter/defibrillator may be subjected to multiple defibrillation shocks, due to an underlying arrhythmia that cannot be converted by the shocks. To achieve this in the first variation of FIGS. 1 and 2, the implanted medical device 12 or 14 would initiate an emergency transmission to the patient communications control device 20 which would contain, but not be limited to, all or some of the following: patient name and mailing address, patient's current medical condition requiring assistance, ongoing "real time physiological variables", patient medical support team information, and current status (patient and device) and data stored within the implanted medical device. The patient communications control device 20 would obtain the GSS signal and transmit all the information to the medical support network 50. The patient may also transmit voice information if conscious of the event. A similar response to an emergency situation can be initiated and completed in the GCMS of the second variation using the modified patient communications control device 20'.

Moreover, patient follow-up and periodic monitoring (i.e. monthly, quarterly, etc.) of the medical implant's stored data and status could be done automatically and be completely transparent to the patient. The medical support team would even have the capability of changing the implanted device settings or programming with complete transparency to the patient (or alternatively, voice or warning signals may be used to identify impending programming).

Interactions with the implanted device and patient may be totally transparent to the patient, e.g., routine location checks to determine if the patient is in proximity sufficiently with the patient communications device to interrogate the implanted device or for follow-up data collection from the implanted device's monitoring memory or reprogramming of operations of the device effected at night while the patient sleeps. Or the patient may be included in the process, even to the extent that voice communications from the staff at the support network to instruct or reassure the patient are received in the patient communications control device.

Variations and modifications to the present invention may be possible given the above disclosure. Although the present invention is described in conjunction with a microprocessor-based architecture, it will be understood that it could be implemented in other technology such as digital logic-based, custom integrated circuit (IC) architecture, if desired.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

What is claimed is:

1. A system for communicating patient device information to and from a medical device adapted to be implanted in an ambulatory patient and with a remote medical support network comprising:
   an implanted device telemetry transceiver within the adapted to be implanted medical device for communicating data and operating instructions to and from the medical device, the implanted device telemetry transceiver having a transceiving range adapted to be extending outside the patient's body when said device is implanted a distance sufficient to receive and transmit such telemetered communications; and
   an external patient communications control device adapted to be located in relation to the patient within the device transceiving range including:
      a system controller for facilitating communications with the implanted medical device;
      an implant wireless interface including a control device telemetry transceiver for receiving and transmitting coded communications between the system controller and the implant device telemetry transceiver;
      a global positioning system coupled to said system controller for providing positioning data identifying the global position of the patient to the system controller; and
      communications means for communicating between the external communications control device and a remote medical support network.

2. The system of claim 1 further comprising:
   communications network interface means coupled to the system controller and the communications means for selectively enabling the communications means for transmitting the positioning data to the medical support network and for selectively receiving commands from the medical support network.

3. The system of claim 2 further comprising:
   an external patient communications device adapted to be located in relation to the patient within the device transceiving range for providing patient voice and data communications with the system controller, so that patient voice communications may be effected through the communications interface means and the communications means with the remote medical support network.

4. The system of claim 3 wherein the communications interface means may effect two-way communication of voice and/or data between the remote medical support network and the patient communications device and implanted device telemetry transceiver.

5. The system of claim 4 wherein said communications means further comprises at least one of the group consisting of:
   a cellular telephone network;
   a satellite-based telecommunication network;
   a hard-wired telephone communications system; and
   a hard-wired interface for computer based system for local area and for modem-based communications systems.

6. A system as set forth in claim 3 further comprising interface means for use by a patient and by which said patient can initiate communications between said external communications device and said remote medical network through patient input to said external patient communications device.

7. The system of claim 2 wherein the communications interface means may effect two-way communication of voice and/or data between the remote medical support network and the patient communications device and implanted device telemetry transceiver by inclusion of cards for accessing one or all of the communications means.

8. The system of claim 7 wherein said communications means further comprises at least one of the group consisting of:
   a cellular telephone network;
   a satellite-based telecommunication network;
   a hard-wired telephone communications system; and
   a hard-wired interface for computer based system for local area and for modem-based e-mail communications systems.

9. The system of claim 2 wherein said communications interface means further comprises:
   portable satellite communications means for interfacing with a satellite based communications network for communicating with said patient communications control device.

10. The system of claim 2 wherein said communications interface means further comprises:
    portable cellular communications means for interfacing with a cellular telephone communications network for communicating with said patient communications control device.

11. The system of claim 2 wherein said communications interface means further comprises:
    hard-wired telephone communications means for interfacing with a telephone communications network for communicating with said patient communications control device.

12. The system of claim 10 wherein said hard-wired telephone communications means is hard-wired to a room telephone outlet of a patient's room for a patient confined to the area of the room.

13. The system of claim 2 wherein said communications interface means further comprises:
    portable personal communications means for interfacing with a telephone communications network for communicating with said patient communications control device.

14. The system of claim 1 wherein: said medical device being adapted to be implanted further comprises:
    storage means for storing programmed operating commands received by said implanted device telemetry transceiver for controlling operations of said implanted device;

means for therapeutically treating the patient in accordance with programmed operating commands;

means for monitoring a patient condition and providing patient condition data; and means for selectively initiating the operation of said therapeutic treatment means and said monitoring means through said operating commands received by said implanted device telemetry transceiver; and said communications means of said patient communications control device further comprises means for receiving operating commands from said communications network interface; and said system controller further comprises means for operating said control telemetry transceiver for transmitting said operating commands to said implantable device telemetry transceiver to thereby store said operating commands in said storage means and effect a commanded operation of said implantable device in response thereto.

15. The system of claim 14 wherein: said medical device being adapted to be implantable further comprises:

means for monitoring a patient condition and providing patient condition data; and means for selectively initiating the operation of said monitoring means through said operating commands received by said implantable device telemetry transceiver; and said system controller further comprises means for operating said control telemetry transceiver for initiating operation of said monitoring means and for telemetering said monitored patient condition data to said patient communications control device transceiver for communication to said medical support network.

16. A system as set forth in claim 1 and further comprising;

real time or continuous clock means in said external patient communications control device for determining instant time, means to coordinate the resetting of clock via a signal received from said GPS system so as to ensure that all external patient communications control devices are in time synchronized operation.

17. A system as set forth in claim 16 wherein each external patient communications control device maintains a memory means for determining when communication by it to said medical network is appropriate and wherein said medical network has means to affect a time instant value stored in said memory means so that said medical network means can optimize a set of non-overlapping time or band location slots for communication with other external patient communications control device.

18. A system as set forth in claim 1 or 17 which further includes means to prevent powerup of the GPS to predetermined times related to times in which communication with said medical network shall occur.

19. A system as set forth in claim 1, 3, or 16 also having patient activated emergency alarm means on said external patient communications control device which instigates communication with said medical network on patient demand.

20. A system as set forth in claim 1 wherein said external patient communications device further comprises a three axis accelerometer and means for interpreting acceleration signals therefrom to establish a patient's motion from a last GPS indicated location.

21. A method for communicating patient device information to and from a medical device implanted in an ambulatory patient and with a remote medical support network comprising:

providing an implanted device telemetry transceiver within the implanted medical device for communicating data and operating instructions to and from the medical device in a coded communication, the implanted device telemetry transceiver having a transceiving range extending outside the patient's body a predetermined distance sufficient to receive and transmit coded telemetry communications at a distance from the patient's body; and providing an external patient communications control device adapted to be located in relation to the patient within the device transceiving range for communicating between the implanted medical device and a medical support network; and responding to an emergency condition of the patient in accordance with the steps of:

receiving global positioning data signals in the communication control device for identifying the global position of the patient to the patient communications control device; and transmitting communication indicating an emergency condition and the global position of the patient from the patient communications control device to the medical support network.

22. A method as set forth in claim 21 comprising the additional step of powering up the communications circuitry only in accord with a predetermined schedule.

23. A method as set forth in claim 22 and further comprising, timing said predetermined schedule so that each patient in the system has a unique time for performing maintenance communications with said medical network.

24. A method as set forth in claim 23 wherein said medical network, when communicated with by each said patient provides a system clock update to said patient's communications circuitry.

25. A method as set forth in claim 21 comprising the additional step of powering up the GPS circuitry to reacquire a GPS location on a periodic basis.

26. The method of claim 21 wherein said step of responding to an emergency condition of the patient in further comprises the step of:

communicating voice messages from said patient to said medical support network.

27. The method of claim 26 wherein said step of responding to an emergency condition of the patient in further comprises the step of:

communicating voice messages to said patient from said medical support network.

28. The method of claim 26 wherein said step of responding to an emergency condition of the patient in further comprises the step of altering an operating mode of said implanted medical device in response to the emergency condition.

29. The method of claim 28 wherein said step of altering an operating mode of said implanted medical device further comprises:

transmitting an operating programming command to said patient communications control device from said medical support network;

in said patient communications control device, transmitting a reprogramming command to said implanted device telemetry transceiver.

30. The process of claim 21 including the step:

in the absence of an emergency patient condition, periodically reporting the location of the patent to the medical network.

31. A method as set forth in claim 21 further comprising the steps of determining a last valid GPS indicated location and storing said location in a memory, Tracking output from a time clock and a three axis accelerometer and storing such output in memory.

computing the current location based on signals received from said three axis accelerometer and from said time clock with reference to the last GPS location.

32. Apparatus for communicating patient device information to and from a medical device adapted to be implanted in an ambulatory patient and with a remote medical support network comprising:

an implanted device telemetry transceiver within the implanted medical device for communicating data and operating instructions to and from the medical device in a coded communication, the implanted device telemetry transceiver having a transceiving range extending outside the patient's body a predetermined distance sufficient to receive and transmit coded telemetry communications at a distance from the patient's body; and an external patient communications control device adapted to be located in relation to the patient within the device transceiving range for communicating between the implanted medical device and a medical support network comprising means for responding to an emergency condition of the patient further comprising:

means for providing positioning data identifying the global position of the patient to the patient communications control device; and means for transmitting an encoded communication indicating an emergency condition and the global position of the patient from the patient communications control device to the medical support network.

33. The apparatus of claim 32 wherein said external patient communications device is adapted to be located in relation to the patient within the device transceiving range and further comprises communications interface means for effecting two-way communication of voice and/or data between the remote medical support network and the patient communications device and implanted device telemetry transceiver.

34. A system for communicating patient device information to and from a medical device adapted to be implanted in an ambulatory patient and with a remote medical support network comprising:

an implanted device telemetry transceiver within the implanted medical device for communicating data and operating instructions to and from the medical device in a coded communication, the implanted device telemetry transceiver having a transceiving range extending outside the patient's body a predetermined distance sufficient to receive and transmit coded telemetry communications at a distance from the patient's body; and an external patient communications device adapted to be located in relation to the patient within the device transceiving range for communicating between the implanted medical device and a communication system.

a medical support network in communicative connection through said communications system with said implanted medical device.

* * * * *